US00PP27288P3

(12) United States Plant Patent
Clark et al.

(10) Patent No.: US PP27,288 P3
(45) Date of Patent: Oct. 18, 2016

(54) COLEUS PLANT NAMED 'UF12-82-3'

(50) Latin Name: *Solenostemon scutellarioides*
Varietal Denomination: UF12-82-3

(71) Applicant: Florida Foundation Seed Producers, Inc., Marianna, FL (US)

(72) Inventors: David G. Clark, Gainesville, FL (US); Grayson M. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/544,561

(22) Filed: Jan. 21, 2015

(65) Prior Publication Data

US 2016/0212903 P1 Jul. 21, 2016

(51) Int. Cl.
*A01H 5/12* (2006.01)

(52) U.S. Cl.
USPC ..... Plt./373

(58) Field of Classification Search
USPC ..... Plt./373
See application file for complete search history.

(56) References Cited

PUBLICATIONS

Rosy Dawn gardens Coleus Campfire. (http://www.rosydawngardens.com/coleus-a-to-d/campfire). Accessed Jan. 14, 2016. 1 page.*
BallFloraPlant Campfire Coleus. (http://www.ballfloraplant.com/series_info.aspx?phid=018000001017661). Accessed Jan. 14, 2016. 1 page.*
FFSP website Cranberry Bog. (http://www.ffsp.net/varieties/coleus/cranberry-bog-uf11-73-8/). Accessed Jan. 14, 2016. 1 page.*
Nguyen et al., "Genetics of growth habit and development of new coleus (*Solenostemon scutellarioides* (L.) Codd) varieties with trailing habit and bright color," *J Heredity* 99:573-580, 2008.

* cited by examiner

*Primary Examiner* — Susan McCormick Ewoldt
*Assistant Examiner* — Karen Redden
(74) *Attorney, Agent, or Firm* — Dentons US LLP

(57) ABSTRACT

'UF12-82-3' is a new coleus plant distinguished by having a combination of novel mounded growth habit, excellent heat tolerance, and lance-shaped leaves consistently colored deep maroon with bright green margins that is significantly different than other coleus plants.

3 Drawing Sheets

Latin name of the genus and species of the plant claimed: *Solenostemon scutellarioides*.

Cultivar denomination: 'UF12-82-3'.

BACKGROUND OF THE INVENTION

The invention relates to a new and distinct cultivar of coleus plant named 'UF12-82-3'. 'UF12-82-3' originated from an open pollination conducted in May-November 2011 in Gainesville, Fla. between the female coleus plant 'UF11-73-8' (unpatented) and an unknown male coleus plant. A single seedling was chosen in May 2012 for further asexual propagation in Gainesville, Fla. (see FIG. 1 for pedigree).

'UF12-82-3' has been reproduced asexually for over one year through vegetative cuttings and has been found to retain its distinctive characteristics through successive asexual propagations. 'UF12-82-3' was first propagated asexually by meristem tip cuttings in May, 2012 in Gainesville, Fla., and has remained true-to-type since that time.

'UF12-82-3' has not been made publicly available more than one year prior to the filing date of this application.

When 'UF12-82-3' is compared to the female parent 'UF11-73-8', both plants have lance-shaped leaves, however 'UF12-82-3' leaves are deeper maroon in color, while 'UF11-73-8' leaves are more orange-red with lemon yellow margins. In addition, 'UF12-82-3' has a more vigorous, lateral, and spreading growth form than 'UF11-73-8'.

When 'UF12-82-3' is compared to the commercial cultivar 'UF08-19-10' (U.S. patent application Ser. No. 14/120,608), both plants have lance-shaped leaves and a well-branched, mounded habit, however 'UF08-19-10' has a red streak through the mid-vein of the leaves, progressing to maroon, then emerald green at the leaf margin, while 'UF12-82-3' does not have a red streak through the mid-vein.

SUMMARY OF THE INVENTION

The following are the most outstanding and distinguishing characteristics of 'UF12-82-3' when grown under normal horticultural practices in Gainesville, Fla. 'UF12-82-3' has a combination of novel mounded growth habit, excellent heat tolerance, and lance-shaped leaves consistently colored deep maroon with bright green margins that is significantly different than other coleus plants. It has superior stability in foliage color in both sun and shade conditions, maintaining stable color in all conditions. It has a vigorous but compact spreading growth habit with excellent lateral branching when grown as a stock plant, thus providing ample vegetative propagules for producers. This plant is desirable for long-season performance in the landscape.

BRIEF DESCRIPTION OF THE DRAWINGS

This new coleus plant is illustrated by the accompanying photographs, which show the plant's form and foliage.

The colors shown are as true as can be reasonably obtained by conventional photographic procedures.

FIG. 2—shows the growth habit, form, and foliage of the claimed plant.

FIG. 3—shows a close-up of the foliage.

DETAILED BOTANICAL DESCRIPTION

Figure 1:
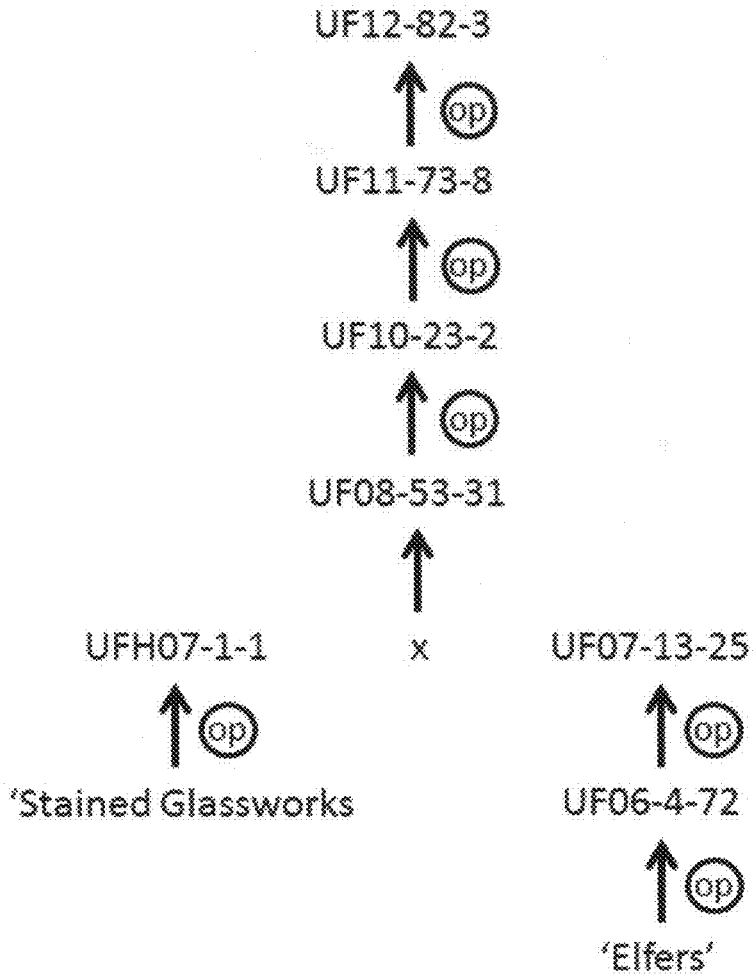
FIG. 1—shows the pedigree of the claimed plant.
Figure 2:
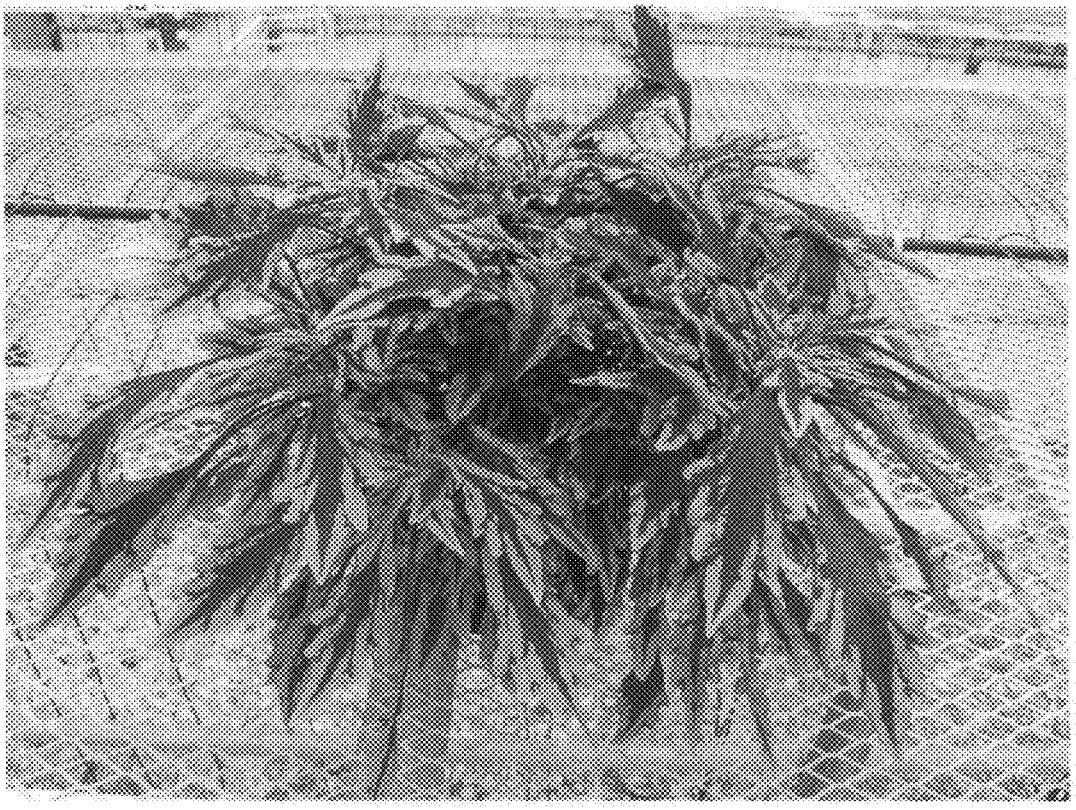
FIGS. 2 and 3 were taken from twelve-week old plants pinched once at four weeks after stick and grown in March-May, 2014 in a glass greenhouse in Gainesville, Fla.
Figure 3:
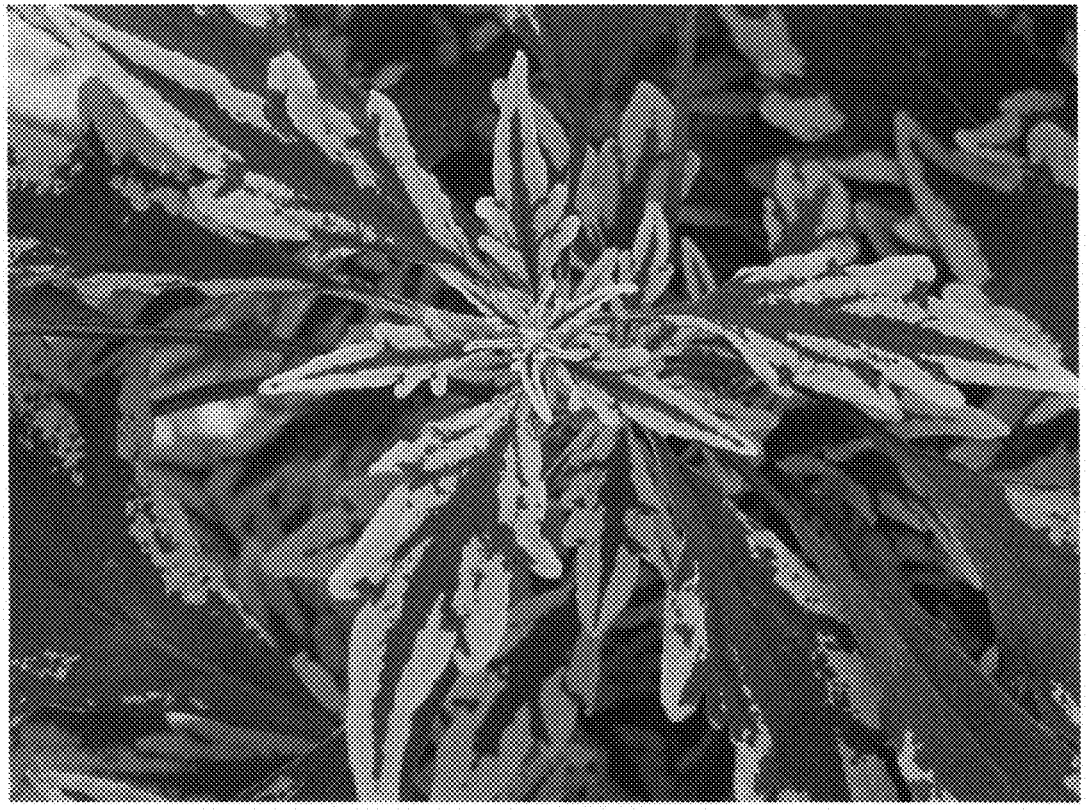

The following detailed description sets forth the distinctive characteristics of 'UF12-82-3'. The detailed description was obtained using twelve-week old plants grown in March-May, 2014 in a glass greenhouse in Gainesville, Fla. The plants were pinched 4 weeks after cuttings were rooted, then grown in 1-gallon pots for approximately 8 weeks. Color references are to The R.H.S. Colour Chart of The Royal Horticultural Society of London (R.H.S.), 2007 5th Edition.

Classification:

*Family*.—Lamiaceae.

*Botanical*.—*Solenostemon scutellarioides*.

*Common name*.—Coleus

*Cultivar name*.—'UF12-82-3'.

Plant description:

*Form*.—Spreading.

*Habit*.—Mounded.

*Height* (*from top of soil*).—25 cm.

*Width* (*horizontal plant diameter*).—55-60 cm.

Propagation:

*Type cuttings*.—Vegetative meristems having at least 1 node.

*Time to initiate roots*.—3-4 days.

*Time to produce a rooted cutting*.—7-10 days.

*Root habit*.—Fibrous.

*Root description*.—Callus forms in 2 to 3 days, roots initiate in 3-4 days and become a highly branched cutting in 7-10 days.

Branches:

*Quantity per plant*.—6-8 main branches per plant with numerous side branches, pinched once.

*Branch color*.—RHS N77A.

*Texture*.—Smooth.

*Pubescence*.—Not present.

*Stem description*.—Square-shaped stem, 1.5 cm in diameter at the soil line.

*Branch diameter*.—0.6-0.7 cm at the base of a 35-cm long branch.

*Branch length*.—25-30 cm.

*Internode length*.—3-4 cm.

*Anthocyanin*.—N/A.

Leaves:

*Quantity of leaves per branch*.—25-30. Arrangement: Whorled.

*Fragrance*.—Not fragrant.

*Shape*.—Elliptic.

*Length*.—9-11 cm.

*Width*.—4-6 cm.

*Apex*.—Abruptly acuminate.

*Base*.—Oblique.

*Margin*.—Lobed.

*Leaf texture* (*both surfaces*).—Slightly pubescent upper surface; smooth lower surface.

*Pubescence color* (*both surfaces*).—Non-descript.

*Venation color*.—Upper surface: Margin-RHS 144A; Center-RHS N77A. Lower surface: RHS N79A.

*Venation pattern*.—Upper surface: Arcuate. Lower surface: Reticulate.

*Color: immature leaf*.—Upper surface: Margin-RHS 144B; Center-RHS N77A. Lower surface: Margin-RHS 144C; Center-RHS 138B.

*Color: mature leaf*.—Upper surface: Margin-RHS 144A; Center-RHS N77A. Lower surface: Margin-RHS 143C; Center-RHS 138A.

*Petiole length*.—7-8 cm.

*Petiole diameter*.—0.2-0.3 cm.

*Petiole color*.—RHS N77A.

*Petiole texture*.—Smooth, no pubescence.

Flowers and seeds: Flowers and seeds have not been observed.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Fla. have been long-tailed or citrus mealybugs (*Pseudococcus* sp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the US is downy mildew (*Peronospora lamii*). This pathogen has been observed in stock materials grown closely together in cooler growing seasons.

What is claimed is:

1. A new and distinct *Solenostemon scutellarioides* plant called 'UF12-82-3' as shown and described herein.

* * * * *